United States Patent [19]

Sang et al.

[11] Patent Number: 5,048,911

[45] Date of Patent: Sep. 17, 1991

[54] COUPLING OF MULTIPLE LASER BEAMS TO A SINGLE OPTICAL FIBER

[75] Inventors: Low K. Sang; Tan B. Cheok, both of Selangor Darul Ehsan, Malaysia

[73] Assignee: Universiti Malaya, Juala Lampur, Malaysia

[21] Appl. No.: 369,621

[22] Filed: Jun. 21, 1989

[30] Foreign Application Priority Data

Nov. 15, 1988 [MY] Malaysia ............... PI8801301

[51] Int. Cl.$^5$ ............................................. G02B 6/32
[52] U.S. Cl. ..................................... 385/33; 372/109; 359/618
[58] Field of Search ............... 219/121.76; 350/96.10, 350/96.15, 96.16, 96.18, 96.20, 96.29, 96.30, 168–174; 372/9, 23, 92, 97, 108, 109; 370/1, 3

[56] References Cited

U.S. PATENT DOCUMENTS

| | | | |
|---|---|---|---|
| 3,953,727 | 4/1976 | D'Auria et al. | 370/3 |
| 4,050,784 | 9/1977 | Kobayashi | 350/96.18 |
| 4,341,438 | 7/1982 | Seki et al. | 350/96.16 |
| 4,344,671 | 8/1982 | Lang | 350/174 |
| 4,566,765 | 1/1986 | Miyauchi et al. | 350/174 X |
| 4,573,465 | 3/1986 | Sugiyama et al. | 219/121.76 X |
| 4,636,611 | 1/1987 | Penney | 350/170 X |
| 4,649,351 | 3/1987 | Veldkamp et al. | 372/97 X |
| 4,655,590 | 4/1987 | Aagano et al. | 219/121.76 X |
| 4,673,290 | 6/1987 | Johnson et al. | 350/171 X |
| 4,714,314 | 12/1987 | Yang et al. | 350/96.20 |
| 4,722,591 | 2/1988 | Haffner | 219/121.76 X |
| 4,725,131 | 2/1988 | Goodwin et al. | 350/96.16 X |
| 4,761,059 | 8/1988 | Yeh et al. | 350/169 X |
| 4,763,975 | 8/1988 | Scifres et al. | 350/96.15 |
| 4,823,357 | 4/1989 | Casey | 350/174 X |
| 4,828,357 | 5/1989 | Arata et al. | 219/121.76 X |

OTHER PUBLICATIONS

C. Perria, T. Capuzzo, G. Cavagnaro, R. Datti, N. Francabiglia, C. Rivano, and V. E. Terocero, "First Attempts at the Photodynamic Treatment of Human Gliomas", Journal of Neurosurgical Sciences, vol. 24, Jul. 1980, pp. 119 to 129.

I. J. Forbes, A. S. Y. Leong, and A. J. Blake, "Phototherapy of Human Tumors Using Hematoporphyrin Derivatives", the Medical Journal of Australia, Nov. 1, 1980, pp. 489 to 493.

I. J. Forbes, A. D. Ward, F. J. Jacka, A. J. Blake, A. G. Swincer, P. A. Wilksch, P. A. Cowled and K. Lee See, "Multidisciplinary Approach to Phototherapy of Human Cancers", Prog. Clin. Biol. Res., 1984, vol. 170, pp. 693 to 708.

J. S. Carruth and A. L. McKenzie, "Preliminary Report of a Pilot Study of Photoradiation Therapy for the Treatment of Superficial Malignancies of the Skin, Head and Neck", European Journal of Surgical Oncology, 1985; vol. 11, pp. 47–50.

*Primary Examiner*—John D. Lee
*Attorney, Agent, or Firm*—Morgan & Finnegan

[57] ABSTRACT

An apparatus and method for coupling a parallel array of laser beams into a single optical fiber. The increased optical laser power, if that of helium-neon lasers, can be used for photodynamic therapy of cancer with hematoporphyrin derivatives.

7 Claims, 4 Drawing Sheets

COUPLING OF MULTIPLE LASER BEAMS TO A SINGLE OPTICAL FIBER

TECHNICAL FIELD

The field of the invention is that of an apparatus and method for coupling a parallel array of laser beams into a single optical fiber for the transmission of higher optical power. If multiple helium-neon lasers, each with a high output power of around 50 mW or more are used, the focussed laser light transmitted in the optical fiber can be applied effectively for photodynamic therapy for cancer treatment.

BACKGROUND ART

It is currently known that photodynamic therapy (PDT) using hematoporphyrin and its derivatives (HpD) requires red light at the wavelength range of around 630 nm. This corresponds to one of the broad absorption maxima of HpD. For FDT applications, red laser outputs from argon ion pumped dye lasers (Forbes et. al., 1980), gold vapour lasers (Forbes et. al., 1984) and helium-neon lasers (Perria et. al., 1980) have been reported. Dye lasers can be tuned to output in the red from 620 to 630 nm whereas the gold vapour laser has an output at 628 nm and the helium-neon laser at 632.8 nm. All three lasers can deliver red laser light equally effectively to an optical fiber for photodynamic therapy. FIG. 1 shows how a simple lens is used to focus a laser beam into an optical glass fiber (typically from 400 to 1000 um diameter) for delivery of red laser light for PDT. Laser output power of a few hundred milliwatts (at least 600 mW as quoted J. A. S. Carruth and A. L. McKenzie, 1985) are necessary. Both the argon ion pumped dye laser and the gold vapour laser can deliver these powers. However, both types of lasers are technically difficult to operate. High electrical power consumption (usually from a 3-phase supply), water cooling, long start up time and elaborate maintenance procedures are needed.

On the other hand, helium-neon lasers are relatively simple lasers to use and can be operated from the usual domestic single phase supply. Helium-neon lasers are also known to be reliable with long operating life. However, presently available commercial helium-neon lasers can give at most 100 mW of stable output power. A single helium-neon laser has therefore too low optical power for practical photodynamic therapy. The possibility of folding a series of helium-neon lasers, either end-on or in folded geometry, has not been reported to be successful due to the difficulties in the alignment of such a long cavity laser due to the small bore size normally required of helium-neon laser tubes. The possibility of using a parallel array of helium-neon lasers, effectively coupled together, has not been conceived as a possible alternative to the dye laser or gold vapour laser systems for photodynamic therapy.

DISCLOSURE OF INVENTION

This invention relates to a parallel array of lasers with a beam delivery system for directing multiple laser beams for focussing into a single optical fiber efficiently. Such an array of lasers, with an arbitrary number of units, can be beam steered and simultaneously focussed into a single optical fiber. If high power helium-neon lasers are used, this arrangement can result in sufficient red laser light power to be focussed into a single fiber and transmitted effectively for photodynamic therapy. Such a helium-neon laser array is easy to operate requiring very little maintenance.

BEST MODE FOR CARRYING OUT THE INVENTION

While it might be known that more than one laser beam can be simultaneously focussed into a single optical fiber, no practical application has been published. Due to the constraints in the physical dimensions of each laser, no scheme has been published for the incoherent addition of multiple laser beams into a single optical fiber.

Figure 1:
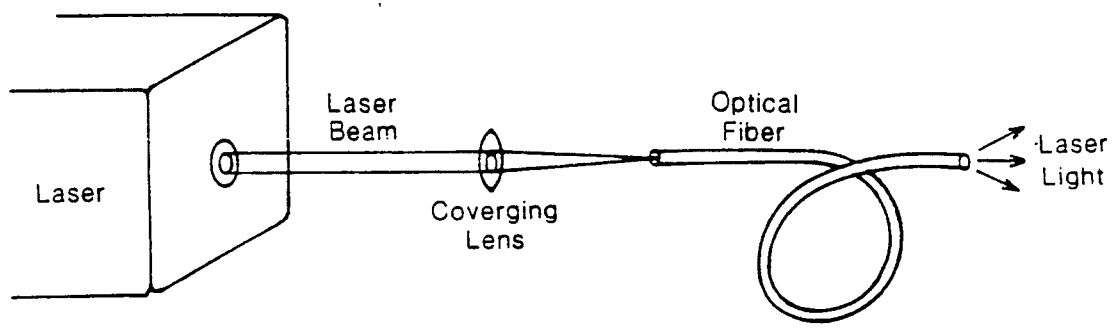
FIG. 1 illustrates a known concept of focussing a single laser beam into an optical fiber.
Figure 2:
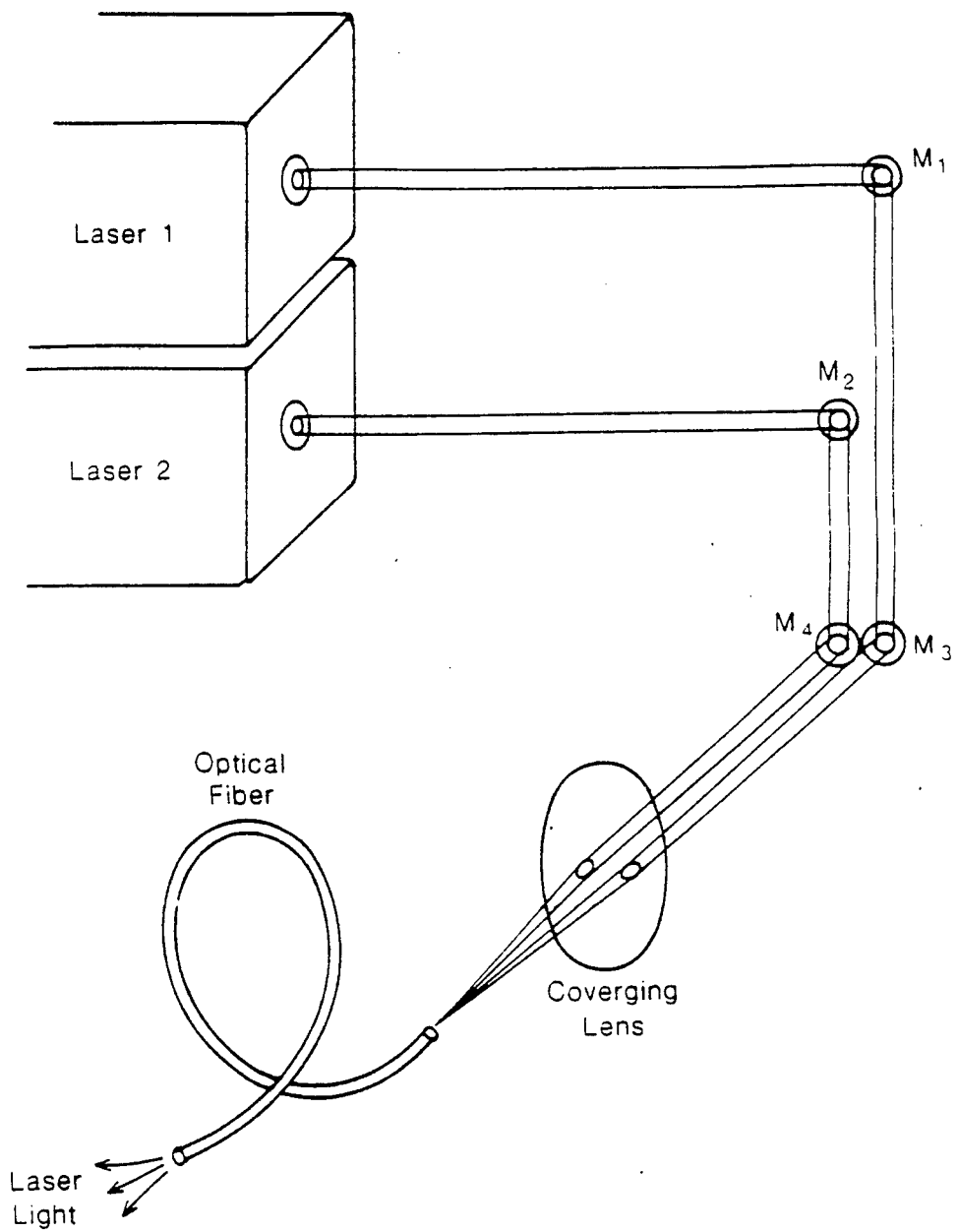
FIG. 2 shows the method of steering a linear array of two laser beams forming two near parallel beams that can be independently steered for focussing completely into a single optical fiber.

FIG. 2 shows how a linear array of 2 laser beams can be beam steered for focussing into a single optical fiber. The arrangement of the 2 beam steering mirrors is paramount to this method. Mirrors M1 and M2 are positioned to enable the two beams to become near parallel and at most two or three millimeters apart, limited by the physical spacing and positioning of the mirrors and their mounts. Mirrors M3 and M4 will enable the directions of the two laser beams to be independently steered through another right angle before incident on the focussing device. While mirrors 3 and 4 can be replaced by a single mirror, the use of two mirrors instead of 1 constitutes a better method due to ease of alignment of the two beams for optimum focussing into the converging device. Since both laser beams can be independently steered, they can be both focussed simultaneously into a single fiber placed at or near the focal point of a light converging device. A converging lens is illustrated although a reflecting concave mirror can similarly be used. The f-number of the focussing device is chosen sufficiently large so that all the converged beams will enter the fiber at an angle smaller than the acceptance angle of the optical fiber used. Further, the fiber diameter has to be chosen sufficiently large so that optimum light acceptance is achieved, taking into considerations the different beam diameters at the focal point due to spherical aberration. The 2 laser beams need not be parallel to the optic axis of the converging device for optimum focussing into the fiber. An aspheric lens or a parabolic mirror can also be used. For maximum coupling of laser light into the fiber, the reflecting mirrors should have the highest reflectivities possible to the laser beams and the converging lens should be anti-reflection coated to the laser wavelength.

Figure 3:
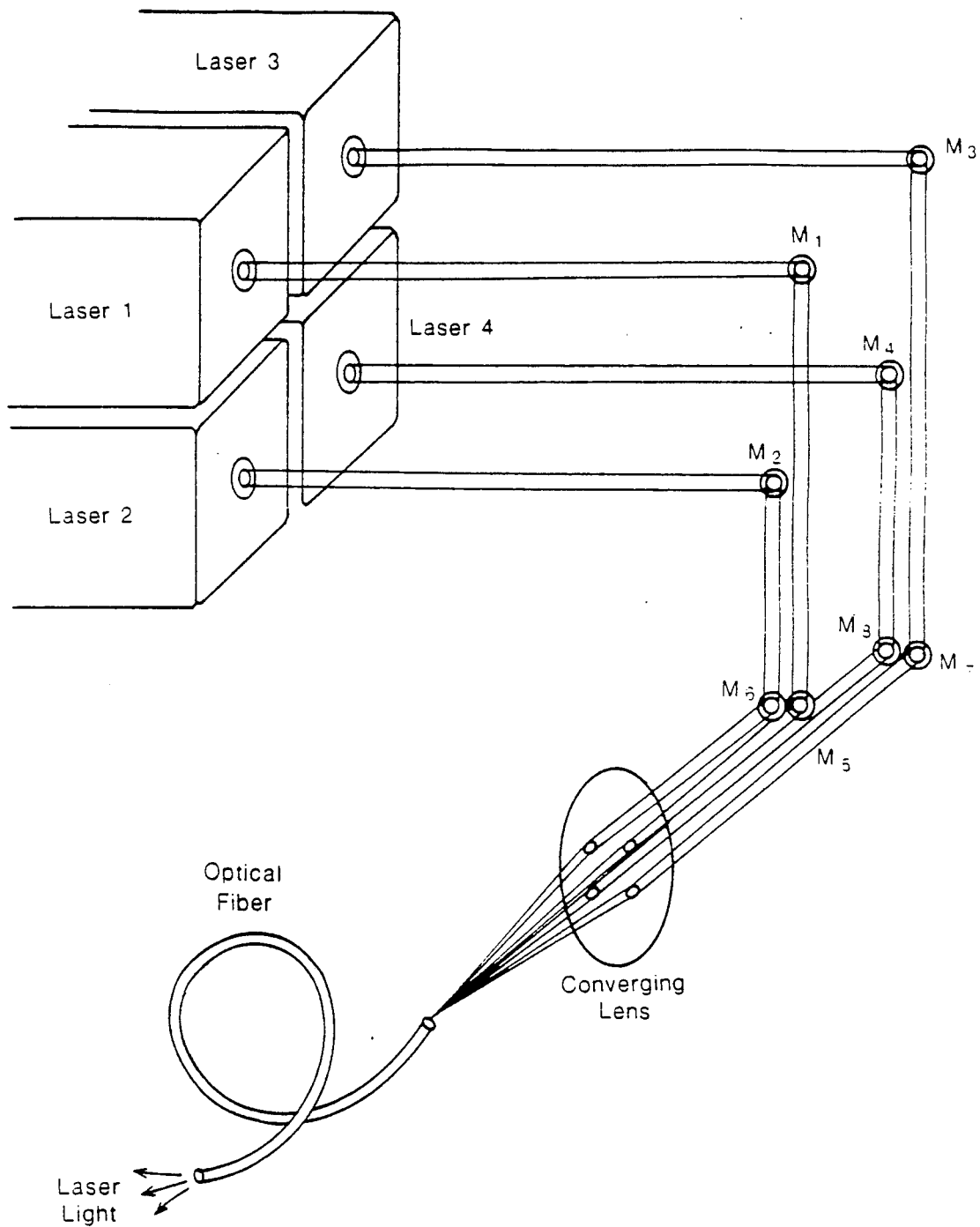
FIG. 3 shows the method of steering a square array of 2×2 laser beams for focussing using a single converging device into a single optical fiber.

FIG. 3 shows how four laser beams, in a square 2×2 array, can be beam steered to be focussed completely into a single optical fiber. Mirrors 1 to 4 enable the four beams, near parallel and physically separated some distance apart, to be brought closer together in one direction as discussed in the case of FIG. 3. Mirrors 5 to 8 enable the beams to be brought closer together in the other direction to form a neatly packed 2×2 laser beams for focussing into the optical fiber. Each of the 4 beams can be independently aligned easily and quickly for maximum coupling into the optical fiber.

Figure 4:
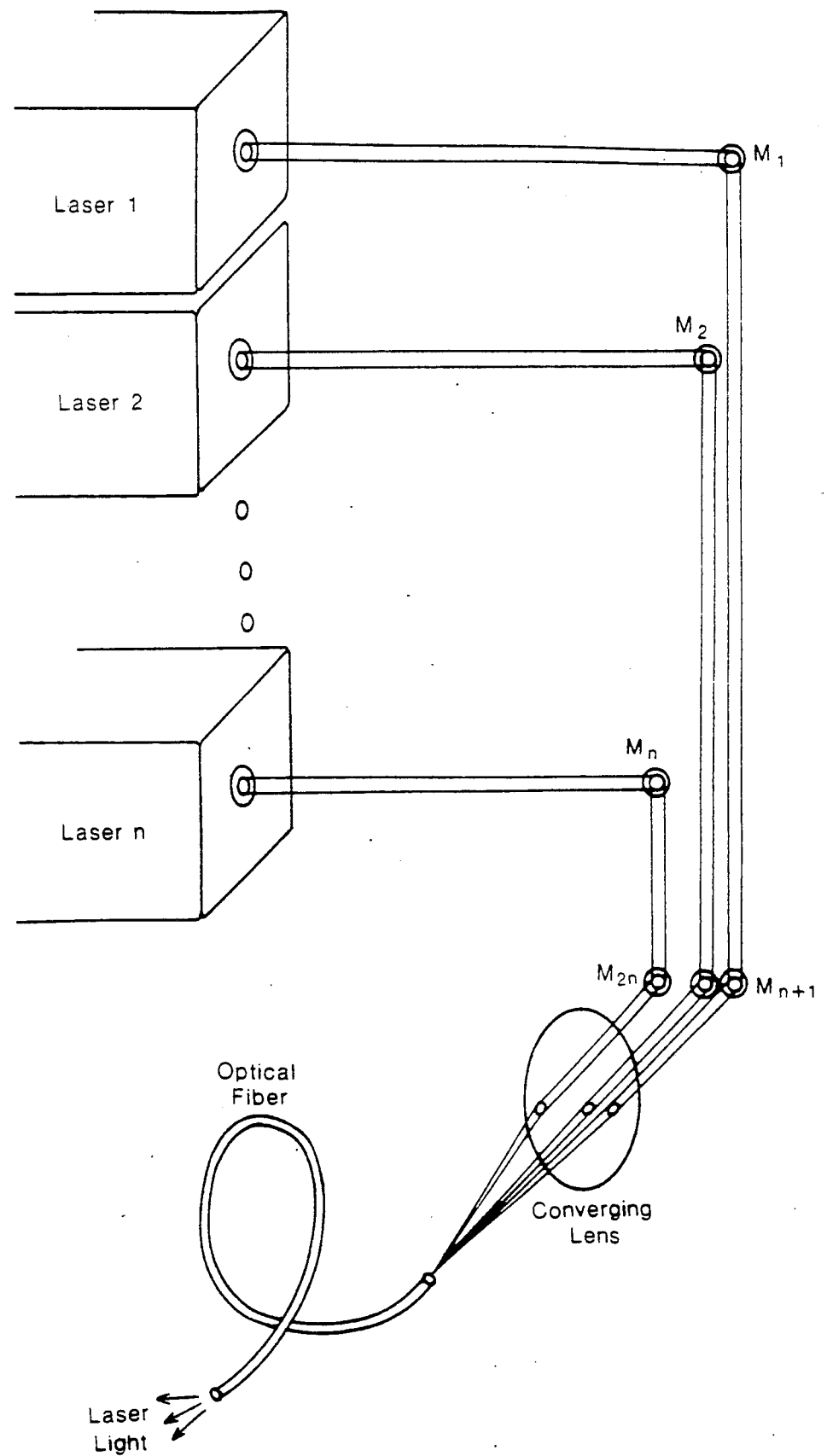
FIG. 4 shows the method of steering a linear array of n×1 array of laser beams for focussing into a single optical fiber.

FIG. 4 shows the generalised method of steering a linear array of n×1 laser beams to become near parallel and very closely spaced laser beams for focussing into a single optical fiber. Miniature mirror mounts are used to ensure that small spacings are obtained between each laser beams.

Based on the methods outlined embodied in the discussions for FIG. 2 and FIG. 3 for the 2×2 laser array, and FIG. 4 for the n×1 linear laser array, any square n×n (n>1) array of laser beams can be generalised and focussed simulataneously into a single optical fiber.

For easier maintenance of the laser array, some of the inner laser positions need not be filled. Thus, for the 3×3 array, the innermost laser should best be left vacant for easier maintenance of the 8 lasers placed on the outside.

STATEMENT OF CLAIMS

While the above describe the best mode of steering a n×n array of laser beams for focussing into a single optical fiber, there are obviously many possible modifications and variations to the arrangement of the beam steering optics with the same end results in light of the above teachings. It is therefore to be understood that within the scope of the appended claims that the invention may be practiced otherwise than as specifically described.

REFERENCES CITED

1. I. J. Forbes et. al., 'Phototherapy of . . . haematoporphyrin derivatives', Med. J. Aust., 1980, 2, 489–493.

2. I. J. Forbes et. al., 'Multidisciplinary approach . . . human cancers', Prog. Clin. Biol. Res., 1984, 170, 693–708.

3. C. Perria et. al., 'Fast attempts . . . human gliomas', J. Neurosurg. Sci. 1980, 24, 119–129.

4. J. A. S. Carruth and A. L. McKenzie, 'Preliminary report . . . head and neck', Eur. J. Surg. Oncol., 1985, 11, 47–50.

What is claimed is:

1. A beam delivery system for photodynamic therapy comprising:
   an optical fiber;
   a plurality of lasers emitting laser beams at substantially similar wavelengths;
   a plurality of beam steering means, each said steering means directing one of said laser beams through at least two right angles to form an array of near parallel beams onto focussing means; and
   said focussing means receiving said steered beams for focussing said steered beams into said optical fiber.

2. The apparatus of claim 1, wherein said plurality of laser beams are produced by a parallel array of high power helium-neon lasers.

3. The apparatus of claim 1, wherein said steering means includes mirrors which direct said laser beams in approximately parallel directions.

4. The apparatus of claim 3, wherein the steered, parallel beams are less than 3 millimeters apart.

5. The apparatus of claim 1, wherein the focussing means has an f-number such that all of the focussed beams will enter the fiber at an angle smaller than the fiber's acceptance angle.

6. The apparatus of claim 5, wherein the focussing means includes a lens.

7. The apparatus of claim 5, wherein the focussing means includes a mirror.

* * * * *

UNITED STATES PATENT AND TRADEMARK OFFICE
CERTIFICATE OF CORRECTION

PATENT NO. : 5,048,911

DATED : September 17, 1991

INVENTOR(S) : Kum Sang Low and Beng Cheok Tan

It is certified that error appears in the above-identified patent and that said Letters Patent is hereby corrected as shown below:

On the cover page, in the heading directly below item [19], "Sang et al." should be -- Low et al. --.

On the cover page, item [75], "Low K. Sang" should be -- Kum Sang Low -- and "Tan B. Cheok" should be -- Beng Cheok Tan --.

Signed and Sealed this

Second Day of March, 1993

*Attest:*

STEPHEN G. KUNIN

*Attesting Officer*     *Acting Commissioner of Patents and Trademarks*